United States Patent

Davison et al.

[11] Patent Number: 5,922,974
[45] Date of Patent: Jul. 13, 1999

[54] GEOCHEMICAL SOIL SAMPLING FOR OIL AND GAS EXPLORATION

[76] Inventors: J. Lynne Davison, 1227 N. Covington, Wichita, Kans. 67212; Billy R. Morris, 407 Carlton Cir., Wichita, Kans. 67209

[21] Appl. No.: 08/887,728

[22] Filed: Jul. 3, 1997

[51] Int. Cl.⁶ .................................................. G01N 1/10
[52] U.S. Cl. ................................... 73/864.74; 73/864.73; 73/863.23
[58] Field of Search ............................ 73/864.74, 863.23, 73/864.73, 864.81, 863.24, 863.21

[56] References Cited

U.S. PATENT DOCUMENTS

| | | | |
|---|---|---|---|
| 3,336,792 | 8/1967 | Boys | 73/23.1 |
| 3,933,431 | 1/1976 | Trujillo et al. | 73/863.23 |
| 4,573,354 | 3/1986 | Voorhees et al. | 73/863.21 |
| 5,000,051 | 3/1991 | Bredemeir | 73/864.74 |
| 5,010,776 | 4/1991 | Lucero et al. | 73/863.23 |
| 5,150,622 | 9/1992 | Vollweiler | 73/864.74 |
| 5,235,863 | 8/1993 | Bailey et al. | 73/863.23 |
| 5,465,628 | 11/1995 | Timmons | 73/864.74 |
| 5,574,230 | 11/1996 | Baugh | 73/863.23 |
| 5,639,956 | 6/1997 | Christy | 73/863.23 |

*Primary Examiner*—Hezron Williams
*Assistant Examiner*—Chad Soliz
*Attorney, Agent, or Firm*—Richard W. Hanes

[57] ABSTRACT

Process and apparatus for extracting soil gases from the earth and analyzing the collected gasses to determine the presence in the soil of gases produced by lower subterranean hydrocarbon deposits, such as petroleum and methane gas. The soil gases are passed from the soil through a soil probe and conductive tubing into a gas collector and concentrator comprising at least one molecular sieve which is chosen and selected for its ability to trap the gas or gases of interest. When the collection and concentration process is completed the gas collector is removed from the field apparatus and taken to a laboratory where the molecular sieves are heated to release the trapped gases. The gases are then analyzed in a gas chromatograph.

1 Claim, 3 Drawing Sheets

GEOCHEMICAL SOIL SAMPLING FOR OIL AND GAS EXPLORATION

BACKGROUND OF THE INVENTION

The present invention relates generally to oil, natural gas and other substances that are encountered in connection with petroleum exploration. More particularly, the invention relates to a method and apparatus for collecting and analyzing particular soil gases which accumulate in the soil above a subterranean deposit of oil and/or natural gas.

An earlier, more primitive version of apparatus for soil gas collection and subsequent chromatographic analysis seen in the F. L. Boys, U.S. Pat. No. 3,336,792. Boys discloses the use of a chromatographic column, lined with molecular sieve material, to identify and quantify the hydrocarbon present in the sample. The soil gas passes into the chromatographic column via a valve, is separated and passed directly to a detector where the amount and character of hydrocarbon gases are determined. The present invention improves on the Boys apparatus by eliminating the need for passing the gas sample directly into the chromatographic column. The apparatus of the present invention provides a gas collector and concentrator which may be detached from the field sampling apparatus and transported to a laboratory for proper analysis of the gases present in the tested soil.

It is therefore the primary object of the present invention to provide apparatus that extracts, collects and concentrates soil gases of particular interest from below the earth's surface and maintains those gasses free from contamination until they are purposefully released for analysis in a properly equipped laboratory away from the field environment.

It is a further purpose and object of the invention to provide a method of extracting, collecting and concentrating soil gases of particular interest and subjecting those gases to analysis at a location removed from the field where the extraction took place.

Other and further objects, features and advantages of the invention will become apparent on a reading of the following specification, taken in conjunction with the accompanying drawings.

DETAILED DESCRIPTION

Figure 1:
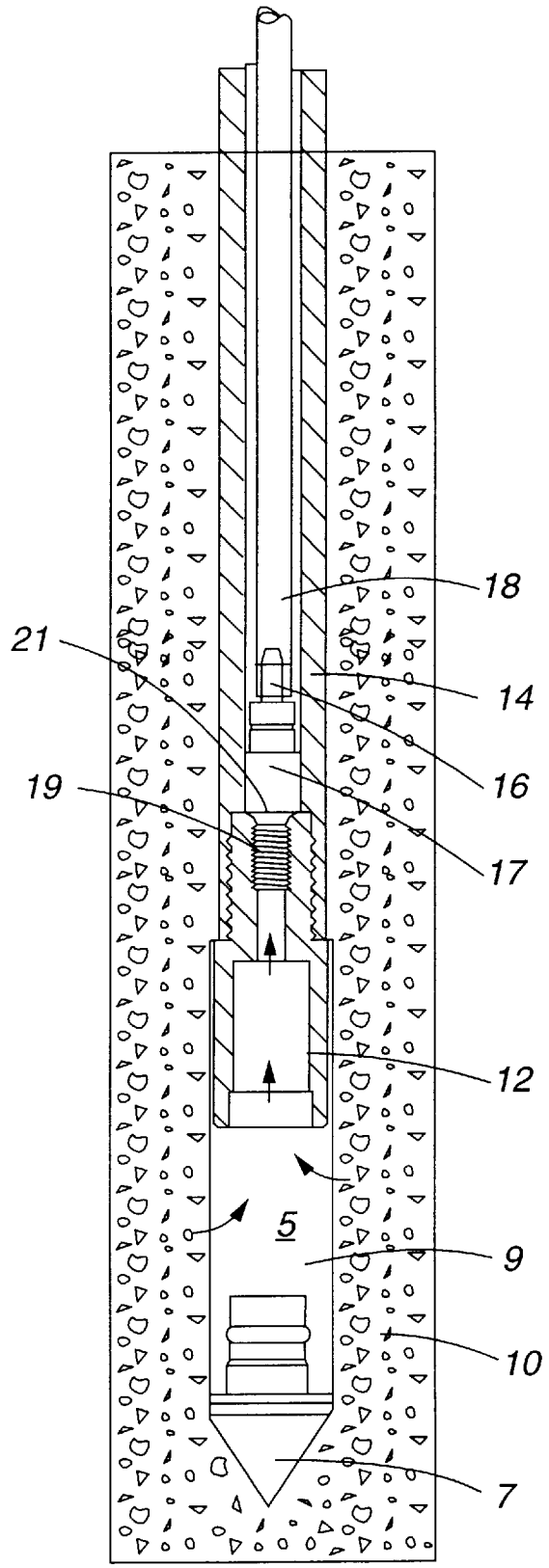
FIG. 1 is a cross-sectional view of a gas conducting soil probe positioned in the earth.

Referring first to FIG. 1, a conventional post-run tubing gas sampling probe is shown. This probe is inserted into the ground by a "direct push" technique which involves the use of a hydraulically powered percussion machine to drive the tool into the ground without having to remove soil and make a path for the tool. The probe tool 5 comprises a point 7, which may be of the retractable or expendable type. Attached to the point 7 is a slotted hollow tube 9 that has a plurality of vents or apertures through which gases emanating from the adjacent soil 10 may enter the hollow interior of the tube. A gas-conducting adapter 12 interconnects the hollow tube 9 with a rigid tubular driving shaft 14. In some cases, depending upon the character of the soil, the hollow tube 9 may be eliminated and the point 7 may be attached directly to the adapter 12 which would, in that case, be provided with vents, apertures, or be opened at the bottom to receive soil gases into the interior of the adapter.

The driving shaft is approximately the same length as the anticipated earth depth of the probe point 7 when it is fully inserted, say ten feet, for example. It is the driving shaft that conducts the hydraulic driving force to position the probe below the surface of the soil being tested. In some cases it is desirable to connect the point 7 directly to the adapter 12. In such a case, after reaching the desired probe depth, the driving shaft 14 is retracted several inches to separate the point 7 from the adapter 12, creating a vertical tunnel in the soil between the probe point 7 and the vented bottom of the adapter., through which soil gases may flow to enter the adapter 12.

The soil gases that enter the interior of the adapter 12 are conducted to a collecting and concentrating device 25, located at the surface, through a flexible tube 18. After the probe tool 5 is positioned at the chosen depth, the lower end of the tube 18 is attached to a nipple 16 at the top end of, and comprising part of, a hollow fitting 17. The fitting contains, at its lower end, a threaded nipple 19, adapted to be screwed into a mating threaded connection disposed in the top end of the adapter 12. The tubing 18 and the attached fitting 17 are placed into the interior of the driving shaft 14 and lowered down to the probe tool's adapter 12 where the threaded nipple 19 is screwed into the threaded connection in the adapter. An "O" ring seal 21, located between the top shoulder of the adapter 12 and an abutment on the underside of the fitting 17, prevents sample contamination from up-hole, and assures that the sample is taken from the desired depth through the gas admitting orifices in the probe tool.

Figure 3:
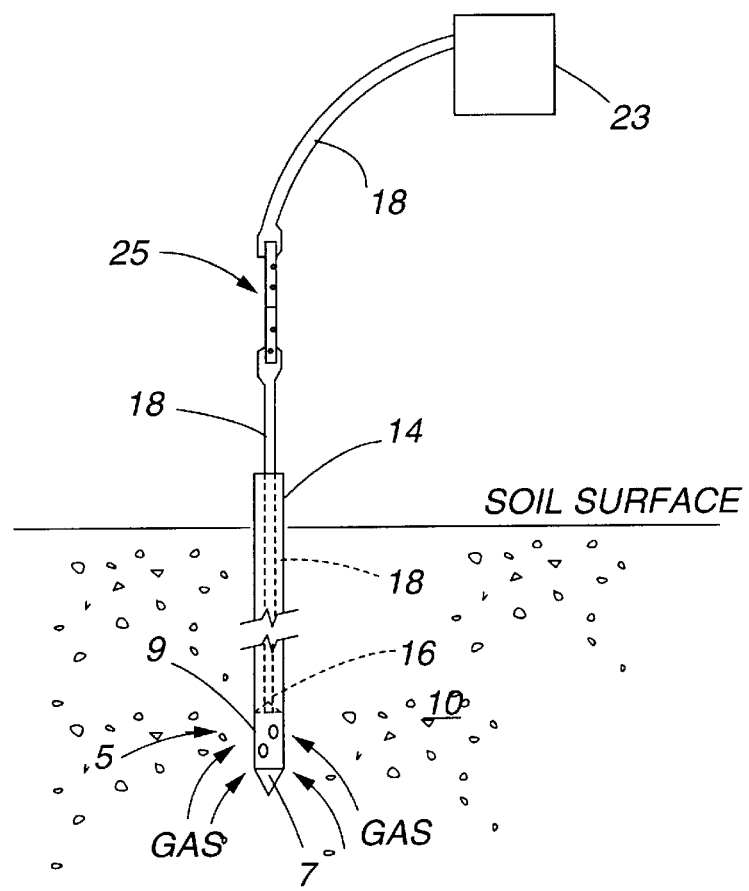
FIG. 3 is a diagrammatic view of the assembled gas extraction and collection apparatus.

Referring to FIG. 3, the tubing 18 is seen to emerge from the top end of the driving shaft 14 at a position above the ground and is connected to a vacuum/volume type of pump 23 that acts to draw the soil gases into the probe tool 5 and upwardly through the tubing 18. Intermediate the point of emergence of the tubing 18 from the driving shaft 14 and the tubing's connection to the vacuum/volume pump 23, a gas collector and concentrator 25 is inserted in series with the tubing so as to comprise a part of the gas flow path from the probe 5 to the pump 23.

Figure 2:
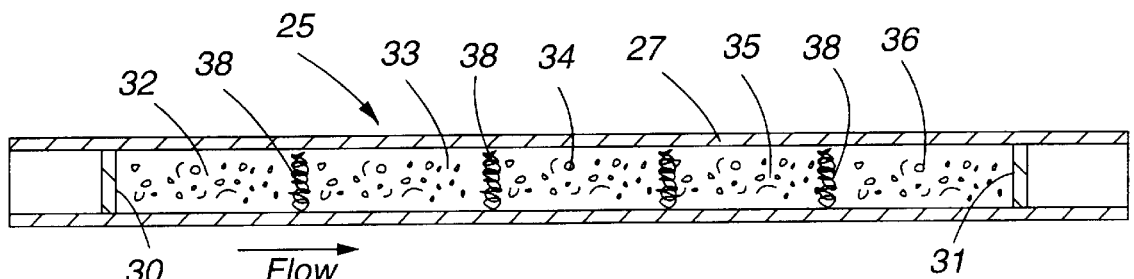
FIG. 2 is a cross-sectional view of the gas collection tube.

The gas collector preferably comprises a glass tube 27 although other suitable tubular materials may serve the purpose. As seen in FIG. 2, the glass tube 27 houses a plurality of different granular materials packed in series within the tube 27, each of which acts as a molecular sieve for the different gases which may be of interest in determining the characteristics of a hydrocarbon deposit possibly positioned below the location at which the probe tool 5 was driven into the ground. A molecular sieve is a material, such as, for example, a resin whose surface pores are of such size as to admit the molecules of a certain gas which are then trapped within the resin until released by heating the resin. By appropriate selection of the resin, a particular gas may be trapped.

As an example of a packed gas collector tube, reference is again made to FIG. 2. Gas permeable glass fritts 30 and 31 act as end retainers to keep the molecular sieves within the tube 27. Proceeding in the direction of gas flow from the probe tool 7, the first packing is a carbotrap 32 for filtering the larger molecules from the sample gas stream. Next in the sequence is a carbosphere 33, acting as a carbon molecular sieve to trap smaller molecular weight hydrocarbons. In gas flow order, the next packings are various synthetic zeolites, or other gas trapping substances, 34, 35 and 36 for retraining the smallest hydrocarbons and other gases. A gas permeable barrier 38, such as glass wool, separates each of the packings. The packings of the tube 27 can be altered to fit the analytical goals of the project, although the packings described above have proved effective in an environment where oil and gas can both occur. If the exploration were for natural gas or helium, the combination of packings might be altered to provide diffusion into the unit cell or crystal lattice of the packing as the trapping method, rather than the pore size of the packing material.

In operation a specific sampling tool and driving shaft is chosen for the probing location, based on soil conditions and the desired depth of the probe. The sampling probe tool 5 is screwed onto the leading end of a one inch diameter hollow steel driving shaft which is advanced into the soil profile using a hydraulic hammer. The down-hole tools including the probe tool, the driving shaft and the hydraulic hammer are conventional pieces of prior art equipment. When the desired depth is reached (7–10 feet normally or soil-bedrock interface) one end of a polyethylene tube 18 is attached to the adapter 12 through the use of the threaded fitting, as explained above. The tubing 18 is purged ¼ liter to remove atmospheric gas via the vacuum/volume pump 23 and it is discarded to the atmosphere. The gas collector 25 is inserted into the gas conducting tubing 18 between the upper end of the driving shaft 14 and the vacuum/volume pump 23. One liter (or any chosen sample volume) is pulled through the packed gas collector tube 27. The light hydrocarbons, such as methane, ethane, propane, butane, pentane, hexane, other hydrocarbons and their isomers, helium and other rare earth gases that may be present in the soil gas sample, are "filtered" out of the soil gas and trapped in the various packings that are contained in the gas sample collector tube 27. At some point, the tube packings can hold no more of the gases being collected and "break-through", or saturation will occur. A better sample can be achieved if break-through does not occur. If a greater sample is desired, two or more gas sample collecting tubes can be placed in series in the tubing line 18 to filter more of the desired gases from a soil gas sample. The collector tube 27 and the packed filtering materials therein act to concentrate the light hydrocarbons found in the soil gas sample. The light hydrocarbons can be concentrated 2, 5, 10, 100 or 1000 times the amount that could be collected by ordinary syringe or cartridge methods of soil gas collection for a traditional analysis on a gas chromatograph.

The vacuum/volume pump 23 is shut off after sampling is complete and the gas sample collector 25, including the collector tube 27, is disconnected from the tubing line 18 after the line pressure returns to ambient atmospheric pressure. The gas collector and concentrating tube 27 is then capped and taken to the lab for thermal desorption.

Figure 4:
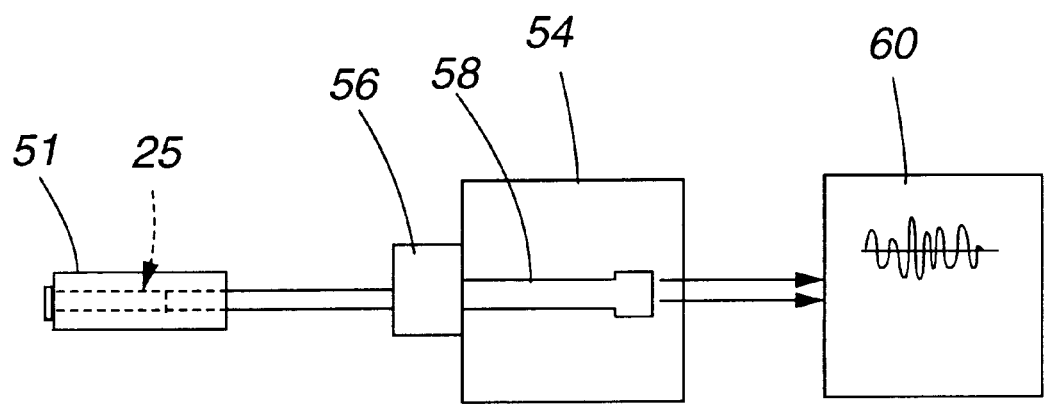
FIG. 4 is a diagrammatic view of the gas collection tube connected to a gas chromatograph in a laboratory setting.

Referring now to FIG. 4, the collection tube 27 is placed in-line in a thermal desorber heater 51. Gases trapped in the "filter" or molecular sieve, along with a carrying gas, such as nitrogen, are directed into a gas chromatograph 54. The head of the gas chromatograph 56 is cooled using liquid $CO_2$ to well below freezing by a cryofocusor and other standard cryo-techniques used in gas chromatography. The hydrocarbon gases retrieved from the molecular sieves pass through the gas chromatograph column 58 and are separated during a 10–20 minute sample run time and plotted on a strip chart recorder 60. The gases are identified and concentrations are determined using various detectors, integrators, and data processors and recorders that are common to all modern gas chromatographic work stations.

We claim:

1. Soil gas sampling apparatus comprising:

a soil penetrating point, an elongated tubular driving shaft, gas conducting means interconnecting the point and the driving shaft, a length of tubing having first and second ends, a portion of which tubing is disposed within the hollow interior of the tubular driving shaft and wherein the first end of the tubing is connected to the said gas conducting means, a vacuum pump connected to the second end of the tubing, exteriorly of the driving shaft, and adapted to draw soil gasses from the gas conducting means through the tubing, gas collection and concentrating means having a gas flow path removably connected in series with the tubing, between the driving shaft and the vacuum pump, said gas collection means further comprising:

a tubular member, a plurality of molecular sieves disposed serially within the tubular member, gas permeable separation means disposed between each of the molecular sieves, and gas permeable retainer means disposed at each of the ends of the series of molecular sieves to retain the sieves within the tubular member.

\* \* \* \* \*